United States Patent [19]
Danssaert et al.

[11] Patent Number: 5,525,300
[45] Date of Patent: Jun. 11, 1996

[54] THERMAL CYCLER INCLUDING A TEMPERATURE GRADIENT BLOCK

[75] Inventors: John L. Danssaert; Robert J. Shopes, both of San Diego; Daniel D. Shoemaker, Stanford, all of Calif.

[73] Assignee: Stratagene, La Jolla, Calif.

[21] Appl. No.: 139,540

[22] Filed: Oct. 20, 1993

[51] Int. Cl.⁶ ..................................................... B01L 7/00
[52] U.S. Cl. ................... 422/99; 422/63; 422/67; 422/104; 435/809; 435/285.1; 435/286.1; 435/286.2; 435/288.4; 435/303.1; 935/85
[58] Field of Search ............................ 422/50, 68.1, 99, 422/104, 109, 67, 63; 435/290, 316, 809; 165/14, 26, 30; 436/43, 47, 49, 174; 935/85

[56] References Cited

U.S. PATENT DOCUMENTS

| | | |
|---|---|---|
| 3,535,208 | 10/1970 | Sasaki et al. |
| 3,770,591 | 11/1973 | Boirat ........................................ 435/809 |
| 3,801,467 | 4/1974 | Nobe et al. ................................ 435/809 |
| 4,865,987 | 9/1989 | Seppo ........................................ 435/290 |
| 4,950,608 | 8/1990 | Kishimoto ................................. 435/290 |
| 4,981,801 | 1/1991 | Suzuki et al. ............................. 435/291 |
| 5,038,852 | 8/1991 | Johnson et al. ............................ 165/12 |
| 5,061,630 | 10/1991 | Knopf et al. ............................... 435/290 |
| 5,133,940 | 7/1992 | Kalkkinen et al. ........................ 435/290 |
| 5,224,536 | 7/1993 | Eigen et al. ............................... 435/290 |
| 5,240,857 | 8/1993 | Lahetkangas ............................ 435/316 |
| 5,255,976 | 10/1993 | Connelly ..................................... 422/99 |

OTHER PUBLICATIONS

Advertisement for Stratagene ROBOCYCLER™Temperature Cycler, 1 page, Jun., 1993.
Advertisement—MJ Research, Inc. Peltier–effect Thermal Cyclers—1page, Jul., 1993.
Advertisement—Appligene Crocodile™II Reactor, 1page, Jul., 1992.
Advertisement—Ericomp PowerBlock™EasyCycler™, 2page, undated.
Advertisement—Biometra UNO–Thermoblock and TRIO––Thermoblock, 1page, 1993.
Advertisement—Corbett Research Fast Capillary Thermal Sequencer, 1page, 1993.
Advertisement—BioTherm Corporation—BioOven II, 1page, 1992.
Perkin Elmer Cetus GeneAmp PCR System 9600 Brochure, 10page, Jul., 1991.
Perkin Elmer Cetus DNA Amplification System Brochures, 11page, Apr., 1990.
Advertisement—Inotech Quarter Bath Immersion Thermal Cycler—1page, undated.
Advertisment—TwinBlock™Thermalcycler, 1page, Jan. 1993.

*Primary Examiner*—Jeffrey R. Snay
*Assistant Examiner*—Jan M. Ludlow
*Attorney, Agent, or Firm*—Limbach & Limbach

[57] ABSTRACT

A method in which a temperature gradient is generated across a "gradient" block, and an apparatus comprising a block across which a temperature gradient can be generated. By setting up such a gradient, multiple reaction mixtures held in wells on the gradient block can be simultaneously run at temperatures which differ only slightly, thereby permitting an optimum temperature for the reaction to be quickly identified. In a preferred embodiment the gradient block is integrated into a thermal cycler used for nucleic acid amplification reactions.

8 Claims, 3 Drawing Sheets

THERMAL CYCLER INCLUDING A TEMPERATURE GRADIENT BLOCK

FIELD OF THE INVENTION

The present invention relates to a temperature cycling apparatus useful for performing nucleic acid amplification, DNA sequencing and the like which apparatus can include single or multiple heating and/or cooling blocks containing sample wells wherein a temperature gradient can be generated across a given block.

BACKGROUND OF THE INVENTION

Systems which require multiple or cyclic chemical reactions to produce a desired product often require careful temperature control to produce optimal results. Such reactions include nucleic acid amplification reactions such as the polymerase chain reaction (PCR) and the ligase chain reaction (LCR). For this reason, apparatus have been developed which permit the accurate control of the temperature of reaction vessels in which such amplification reactions are performed.

For example, there are a number of thermal "cyclers" used for DNA amplification and sequencing in the prior art in which one or more temperature controlled elements or "blocks" hold the reaction mixture, and the temperature of a block is varied over time.

Another prior art system is represented by a temperature cycler in which multiple temperature controlled blocks are kept at different desired temperatures and a robotic arm is utilized to move reaction mixtures from block to block.

All of these systems include features which allow the user to program temperatures or temperature profiles over time for a block on the instrument so that various processes (e.g. denaturing, annealing and extension) can be efficiently accomplished once the optimum temperatures for these steps are determined. Importantly, however, the determination of the optimum temperature for each of the various steps in any reaction system, and in particular for any nucleic amplification or incubation reaction involving an annealing step, is not a simple task.

PCR is a technique involving multiple cycles that results in the geometric amplification of certain polynucleotide sequence each time a cycle is completed. The technique of PCR is well known to the person of average skill in the art of molecular biology. The technique of PCR is described in many books, including, *PCR: A Practical Approach,* M.J. McPherson, et al., IRL Press (1991), PCR Protocols: *A Guide to Methods and Applications,* by Innis, et al., Academic Press (1990), and *PCR Technology: Principals and Applications for DNA Amplification,* H.A. Erlich, Stockton Press (1989). PCR is also described in many U.S. patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, which are hereby incorporated by reference.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle. As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

The temperature of the reaction mixture must be varied during a PCR cycle, and consequently varied many times during a multicycle PCR experiment. For example, denaturation of DNA typically takes place at around 90°–95° C., annealing a primer to the denatured DNA is typically performed at around 40°–60° C., and the step of extending the annealed primers with a polymerase is typically performed at around 70°–75° C. Each of these steps has an optimal temperature for obtaining the desired result. Many experiments are required to determine the optimal temperature for each step.

For example, while the temperature at which DNA denatures is generally between 90°–95° C., slight variations in the particular temperature necessary are observed depending on the length of the DNA and the percentage of each of the four deoxynucleotides present (guanine-cytosine pairs and adenine-thymine pairs). Insufficient heating during the denaturation step is a common reason for a PCR reaction to fail. However, overheating during the denaturation step can result in excessive denaturation of the polymerase.

Achieving the optimal temperature for the PCR annealing step is even more critical. An annealing temperature which is too low will result in nonspecific DNA fragments being amplified. At too high of an annealing temperature, the primers will anneal less efficiently resulting in decreased yield of the desired product and possibly reduced purity. In the annealing step, the optimal temperature will depend on many factors including the length of the primer and the percentage of each of the four deoxynucleotides present (guanine-cytosine pairs and adenine-thymine pairs). For a typical 20-base oligonucleotide primer comprised of roughly 50% guanine-cytosine, a temperature of 55° C. is a good estimate for the lower end of the temperature range. However, as one increases the primer length in order to attain greater primer specificity, differing annealing temperatures may be required. Thus, the number of subtle influences on the optimal annealing temperature makes difficult the task of quickly identifying the optimum for a given system.

Achieving the optimal temperature for the extension reaction is also important for obtaining the desired PCR result. Temperature may affect both the rate and the accuracy of the extension reaction. If the rate of the polymerase reaction is too low, then the newly synthesized polynucleotide may not contain a site for primer annealing. Additionally, the denatured polynucleotide sequence for amplification may contain one or more regions of secondary structure that may form or disappear according to the temperature selected. Furthermore, several different enzymes with polymerase activity may be used for PCR. Each enzyme will have its own optimum temperature for activity, stability and accuracy.

Determination of the optimal denaturing, annealing, and extension temperatures for a particular PCR is complicated by the fact that the optimum will be different for each of the reactions. Thus, in order to determine the three optimal temperature ranges, multiple separate experiments must be run where two temperature variables are held constant while a third temperature variable is changed. As a result, determination of the optimal temperature for running a PCR system can be a time consuming task.

It is therefore an object of the present invention to provide an efficient means by which optimal reaction temperatures can be more efficiently identified for PCR and other reactions.

SUMMARY OF THE INVENTION

To achieve this object, the invention is a method in which a temperature gradient is generated across a "gradient" block. The invention also includes an apparatus comprising a block across which a temperature gradient can be generated. By setting up such a gradient, multiple reaction mixtures can be simultaneously run at temperatures which differ only slightly, thereby permitting an optimum temperature for a given reaction to be quickly identified. In the most preferred embodiment of the invention the gradient block is integrated into a thermal cycler. By doing so, it is possible to run a series of desired reactions using the thermal cycler immediately upon identification of the optimum reaction temperature.

In a first embodiment, the invention is a method for simultaneously reacting a plurality of reaction mixtures in an apparatus including a temperature gradient block comprising the steps of:

placing reaction mixtures in a plurality of reaction wells in the gradient block, the gradient block having a top portion, first and second oppposing portions, and a bottom portion, the plurality of reaction mixture wells being formed in the block between the opposing portions, and generating a temperature gradient across said gradient block and between the opposing portions.

In this embodiment, the step of generating a temperature gradient may comprise the steps of heating the first opposing portion of the gradient block, and cooling the second opposing portion of the gradient block. The method may also include the step of controlling the temperature gradient using a controlling means. By using a controlling means, the method may further include the steps of collecting and storing temperature set point and actual temperature data from the wells, and transmitting that information to a microprocessor.

In another form of the method of the invention, where the apparatus further comprises at least one additional heat conducting block having a top portion, first and second opposing portions, and a bottom portion, and a plurality of reaction mixture wells formed in the additional block between the opposing portions, the method may further comprise the step of moving the reaction mixtures between the gradient block and one or more of the additional block or blocks.

In another form, the method employs an apparatus comprising at least one heat conducting block, the block having a plurality of sample wells spaced between first and second opposing portions and in an upper surface thereof, and the method comprises placing reaction mixtures in the wells, and generating a temperature gradient across the block and between the opposing portions by heating the first opposing portion and cooling the second opposing portion.

The invention also includes an apparatus comprising:

a reaction mixture holder, the reaction mixture holder comprising a heat conducting block having a top portion, first and second opposing portions, and a bottom portion, a plurality of reaction mixture wells formed in the top portion, and between the first and second opposing portions, a block heater positioned adjacent to the first opposing portion, and a block cooler positioned adjacent to the second opposing portion.

In another form, the apparatus of the invention comprises holding means for holding a reaction mixture, the holding means including a heat conducting block having a top portion, first and second opposing portions, and a bottom portion, and a plurality of reaction mixture wells formed in the top portion and between the first and second opposing portions; and means for generating a temperature gradient across the heat conducting block and between the first and second opposing portions.

In yet another form, the invention includes an apparatus for performing molecular biological reactions comprising at least one temperature controlled block, the block having a plurality of reaction mixture wells spaced between first and second opposing portions and in an upper portion thereof, and a block heater positioned adjacent to the first opposing portion and capable of generating a temperature gradient between the first and second opposing portions.

In a preferred embodiment, the heat conducting block or "gradient" block is made substantially of, or comprises, brass.

The apparatus of the invention can include additional elements. Thus, in an especially preferred embodiment, the apparatus includes more than one heat conducting block along with the gradient block. The apparatus may also include a controller for controlling the temperature gradient across the gradient block, and in a multi-block apparatus, the controller may also control the temperature of blocks which are heated or cooled to a uniform temperature. Preferably, the controller will include a microprocessor for collecting and storing temperature set point and actual temperature data, and multiple temperature sensors for collecting the actual temperature data from the wells and for transmitting the information to the microprocessor.

In another embodiment, the plurality of wells in the gradient block are formed in parallel, aligned rows. Further, where more than one block is included, the apparatus may include a robot arm for moving samples between blocks in a programmably controllable manner.

BRIEF DESCRIPTION OF THE DRAWINGS

The invention will be better understood by reference to the appended figures of which.

DETAILED DESCRIPTION OF THE INVENTION

The present invention relates to a device and method for creating a thermal gradient across a block, such as a block in known thermal cyclers for PCR reactions, which enables one to simultaneously conduct a series of experiments at very close to the same temperatures. As used herein, the term "block" refers to a structure, usually metal, which can be temperature controlled and in which wells have been arranged to accept vessels containing reaction mixtures or "samples." The phrase "gradient block" as used herein is intended to describe such a block, except that a gradient block is a block across which a temperature gradient can be established. Examples of the specific manner in which such a temperature gradient can be established are discussed herein, though those skilled in the art will understand that once the advantage of having a gradient block is known, many other variations of the apparatus shown herein can be easily identified.

One particular area of utility for the present invention is in multiple block thermal cyclers. By incorporating the gradient block of the invention into a multiple block thermal cycler, it is possible to simultaneously conduct a series of reactions where the temperature at which the reactions are proceeding is varied across the gradient block. This permits the rapid determination of the optimal temperature for that particular reaction.

Figure 1:
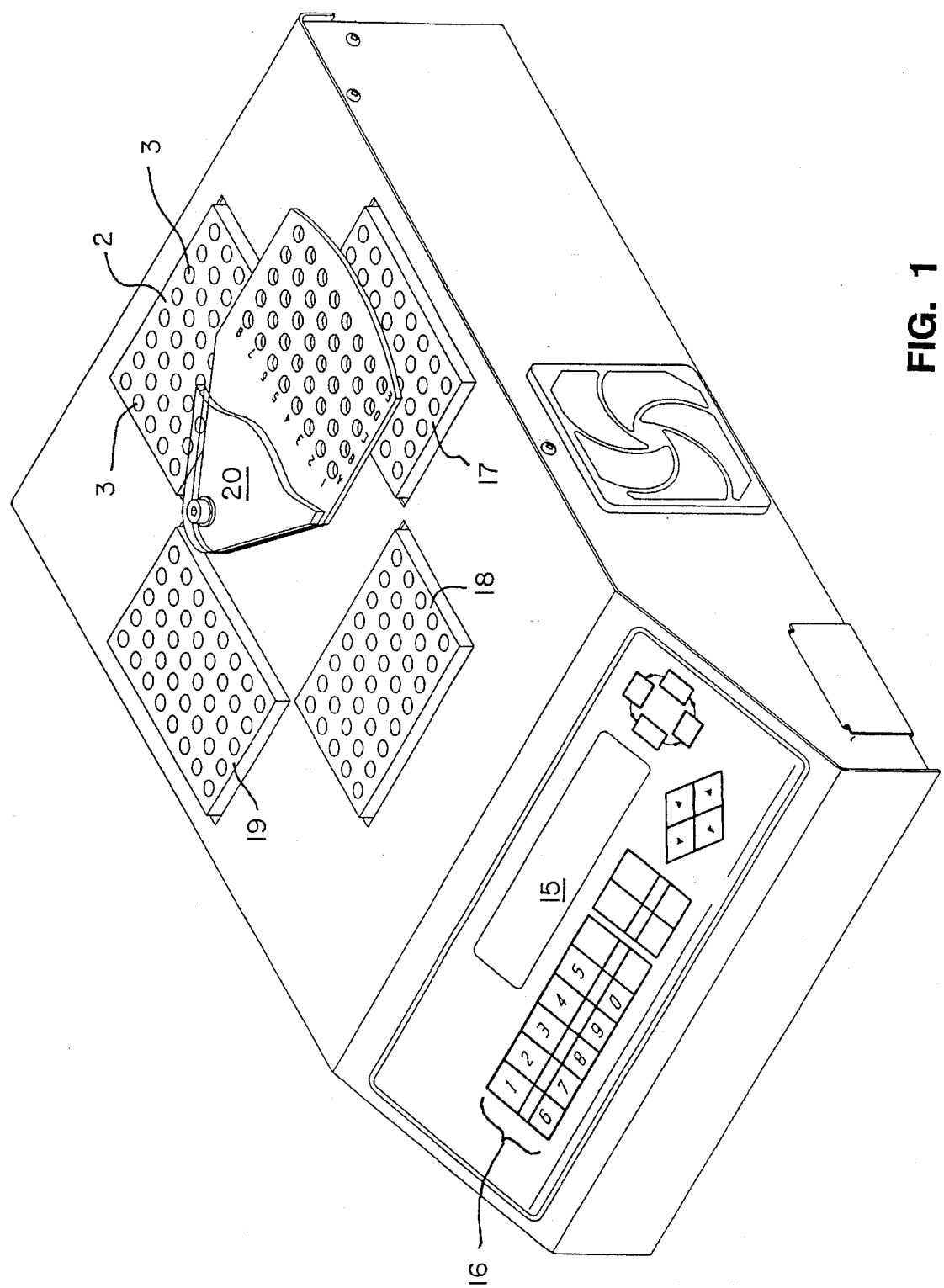
FIG. 1 is a perspective view of a thermal cycler incorporating the thermal gradient block of the invention.

FIG. 1 depicts the prior art Stratagene device in which a thermal gradient block 2 according to the invention has been incorporated.

Figure 2:
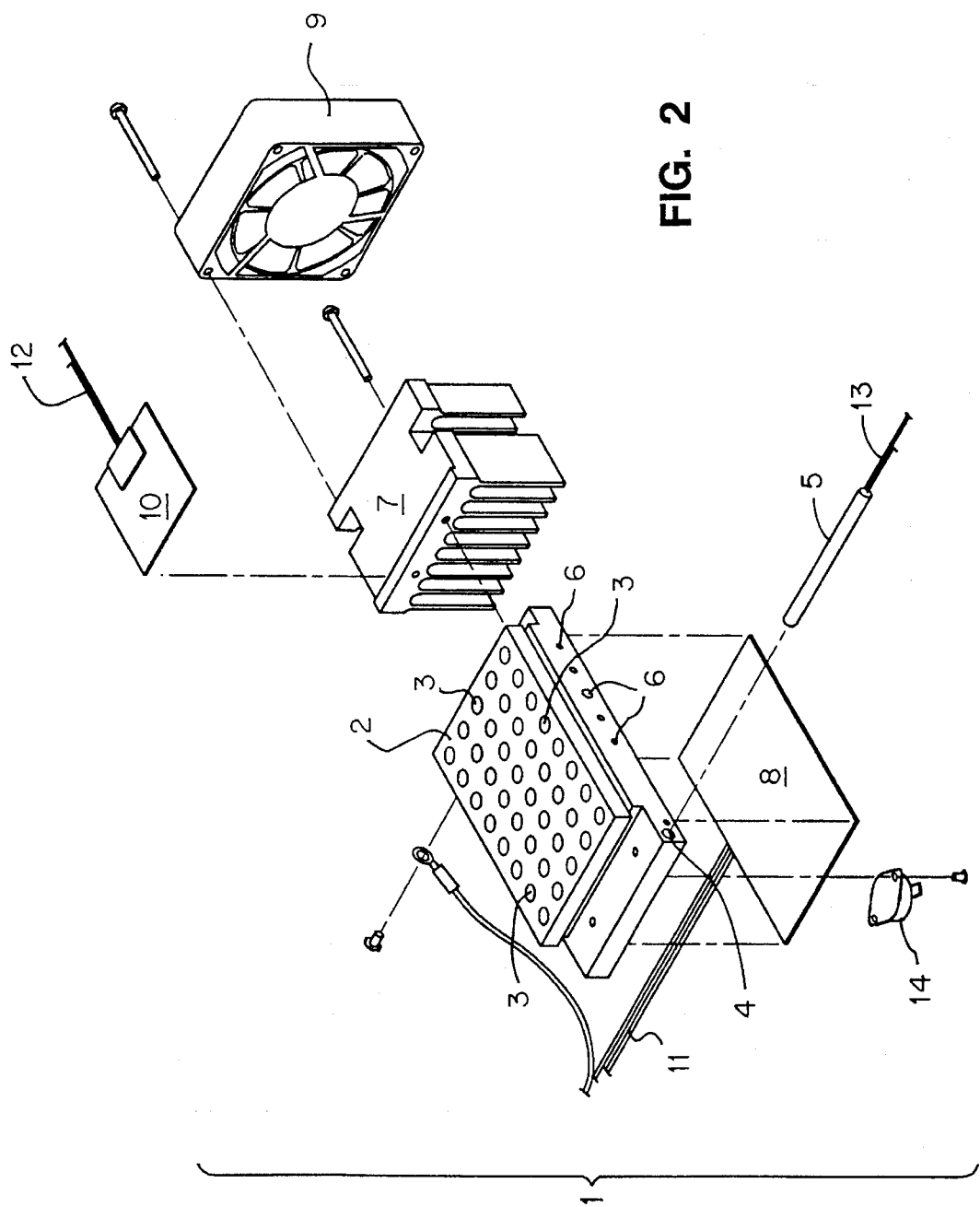
FIG. 2 is a perspective, exploded view, of the thermal gradient block, surrounding heaters and cooler according to the invention.
Figure 3:
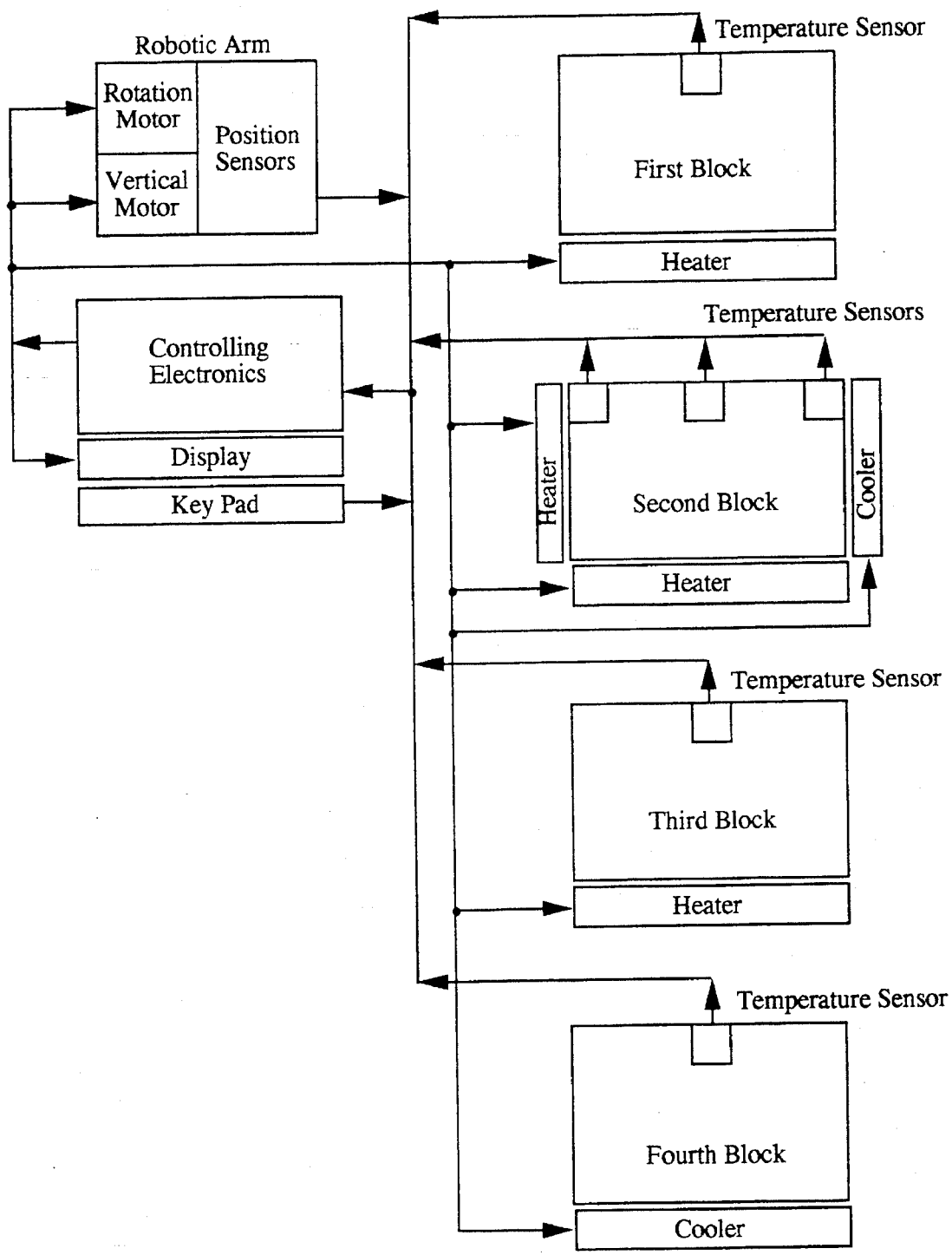
FIG. 3 is a block diagram depicting the elements of a thermal cycler in which the thermal gradient apparatus and method of the invention may be used.

Various components of the cycler depicted in greater detail in FIGS. 2 and 3 can be seen in FIG. 1, i.e. display 15, keypad 16, additional blocks 17, 18 and 19 and robot arm 20 (shown in cutaway view).

It will be understood that a microprocessor can be incorporated into the control electronics of the apparatus, as is well known. The microprocessor can be used to control the range of the temperature gradient and also to program the movement of samples into and out of the thermal gradient block. The microprocessor executes commands written in software that collect user input via the keyboard, compare the input to actual temperatures, and turn off or on the heating or cooling units as appropriate. The electronics also includes a timer, readable by the microprocessor. This allows the microprocessor to compare the elapsed time that the reaction mixture has been in a given block and compare it to a desired time input by the user.

The microprocessor will also control the robot arm, which arm is operated using two stepper motors. One motor raises and lowers the arm. The other rotates the arm from block to block.

Thus, those skilled in the art can readily understand how the thermal gradient block of the invention can be incorporated into known thermal cyclers.

Of course, the thermal gradient block of the invention need not necessarily be incorporated into a known cycler to be advantageously used. For example, a stand alone unit incorporating the thermal gradient block could be used in conjunction with known cyclers so that optimum reaction temperatures could be identified and then used in those cyclers.

FIG. 2 provides an exploded view of the components of the gradient block assembly. Thus, in FIG. 2, the gradient block apparatus is generally designated by reference number 1. The apparatus comprises a heat conducting block 2 which incorporates a number of wells 3 for holding reaction mixtures or the vessels in which the mixtures can be held. In a portion of block 2, heater 5 fits into opening 4. Heater 5 is a commonly available cylindrically shaped cartridge type resistive heater (RAMA brand, San Jacinto, Calif.).

Depending on the temperature range desired, the opposing portion of block 2 may simultaneously be cooled using a heat sink made up of a ribbed aluminum block 7 and a fan 9. Naturally, whether the heat sink is operated or not, a temperature gradient will be created between the opposing portions of the block. However, where the temperature gradient is to be made larger, the heat sink can be operated. To enhance the ability to create and maintain a gradient, block 2 is preferably composed of a material with a relatively low coefficient of thermal conductivity to reduce the amount of heat flux necessary to create the temperature gradient across the block. Brass is preferred.

Where a multiblock system is used (FIG. 1) blocks other than the gradient block will be constructed of a material with a relatively high coefficient of thermal conductivity. By doing so, the blocks can be heated or cooled to a uniform temperature but will not be thermally conductive enough to require excess heating or cooling to maintain a temperature. Aluminum is known for such uses in the prior art.

Depending on the size of the gradient block and the heating and cooling capacities of the heater and heat sink, temperature gradients in excess of 1° to 14° C. across block 2 can be achieved. Holes 6 may be drilled in block 2 between the parallel aligned rows of wells. The holes 6 extend through the block 2 from one side wall to the other side wall. The holes 6 limit thermal conductivity, such that each row of wells in the block tends to be at one temperature. The use of holes also permits the temperature profile across the gradient block, and from one row of wells to the next, to be linear.

Heaters and coolers known in the art may be used. For example, Peltier thermoelectric devices may be used, though other passive or active heaters would also be useful (e.g. chilled or heated liquids or gases).

As shown in both FIGS. 1 and 2, gradient block 2 preferably has eight rows of sample wells 3 equally spaced across the block. Each row can contain five sample wells. 0.5 ml tubes can be used. The particular number and design of the sample wells can be varied to modify capacity if desired. If a temperature gradient of 8° C. is formed between the hot and cold portions of the block, each row of sample wells will differ in temperature by approximately 1° C.

Returning to FIG. 2, additional heaters 8 and 10 may also be employed so that the system can be operated in the same manner as blocks known in the art, i.e. with uniform heating across the entire length and width of block 2. Heaters 8 and 10 are preferrably thin foil type (MINCO brand Minneapolis, Minn.). Heaters 8 and 10 can also be in conjunction with heater 5 to bring block 2 to at least the cool portion temperature as quickly as possible when the system is started or the temperature range over which block 2 is to be operated is raised.

Wire connectors 11, 12 and 13 connect the heaters to a power source. Apparatus 1 may also include a thermostat 14 which can be used as a high temperature cut-off, which is a desirable safety feature.

The block diagram of FIG. 3 depicts a gradient block (labelled "second block") of the type shown in FIG. 2 as block 2 integrated into a thermal cycler having multiple heating and cooling blocks. The labels in FIG. 3 are self-explanatory, and the apparatus described by FIG. 2 differs from a known thermal cycler only with respect to the substitution of the gradient block for a non-gradient block. For PCR, the first, second and third blocks in FIG. 3 may be programmed to be maintained at a temperature range of between about 25° to 99° C., and are used for denaturing, annealing and extension respectively. The fourth block is generally maintained at between 4° and 25° C. and is used for sample storage after the PCR reaction has completed. The second block, made of brass, will be used for the annealing step.

As can be seen in FIG. 3, more than one thermocouple can be used along the length of the gradient block so that temperatures along the block can be carefully monitored and used to feed information back to the control electronics and display.

The following examples are offered for the purpose of illustrating, not limiting, the subject invention.

EXAMPLE 1

USE OF THE GRADIENT THERMAL CYCLER FOR THE POLYMERASE CHAIN REACTION

High temperature primer extension testing of the thermal gradient system of the invention was carried out using two model primer/template systems. These two systems exhibit significantly variable extension product yields depending upon the annealing temperature used during the extension process. Primer/template set #1 amplifies a 105 bp region of the human Gaucher gene, while set #2 amplifies a 540 bp region of the human fucosidase geneo The thermal gradient system of the invention contains a gradient block that allowed primer extension using an optimal annealing temperature range of 42° to 56° C.

METHODS AND MATERIALS

Primer extension reactions were carried out using the gradient block of the invention. Primer/template test set #1 consisted of a genomic human DNA template and two 22 mer oligomers yielding a 105 bp extension product. The sequence of primer A was 5' CCTGAGGGCTCCCA-GAGAGTGG 3'9 (SEQ ID NO:1). The sequence of primer B was 5' GGTTTAGCACGACCACAACAGC 3'(SEQ ID NO:2). Primer/template test set #2 consisted of a genomic human DNA template and two oligomers of 20 and 30 bases respectively yielding a 540 bp extension product. The sequence of primer A was 5' AGTCAGGTATCTTTGA-CAGT 3' (SEQ ID NO:3). The sequence of primer B was 5' AAGCTTCAGGAAAACAGTGAGCAGCGCCTC    3' (SEQ ID NO:4).

The primer extension reaction mixture consisted of 1X Taq DNA polymerase buffer (10 mM tris-HCl pH 8.8, 50 mM KCl, 1.5 mM MgC12, 0.001% (w/v) gelatin), 250 uM each dNTP, 250 ng each primer and template and 2.5 units Taq DNA polymerase in a 100 μl reaction volume. The reaction mixture was overlayed with 50 μl of nuclease free sterile mineral oil.

The temperature cycling parameters used were as follows:

| | | |
|---|---|---|
| 1 min | 94° C. | |
| 1 min | 42–56° C. (gradient block) | |
| 1 min | 72° C. | |
| 1 min | 94° C. | 30 cycles |
| 1 min | 42–56° C. (gradient block) | |
| 8 min | 72° C. | |
| Storage | 4° C. | |

Eight reaction mixes were tested per primer/template set— one per gradient temperature block slot. Annealing temperatures used were 42°, 44°, 46°, 48°, 50°, 52°, 54° and 56° C. (two degree C increments across the gradient block). Reactions were carried out in 500 μl eppendorf tubes.

RESULTS

Both primer/template sets 1 and 2 yielded obviously varying results depending upon the annealing temperature used in the gradient temperature block. Primer extension products from set #1 varied from the desired single DNA band of size 105 bp (derived from the extension reaction using a 56° C. annealing temperature) to a reaction mix yielding multiply sized extraneous DNA extension products (of approximate size 180, 280 and 800 bp) from a reaction using a 48° C. annealing temperature. Primer extension products from set #2 varied from the desired single DNA band of size 540 bp (derived from the extension reaction using a 42° C. annealing temperature) to a reaction mix yielding an extraneous DNA extension product of approximately 2000 bp from a reaction using a 56° C. annealing temperature.

EXAMPLE 2

USE OF THE GRADIENT THERMAL CYCLER FOR THE LIGASE CHAIN REACTION

Ligase chain reaction (LCR) is a recently described DNA amplification technique that can be used to detect trace levels of known nucleic acid sequences. LCR involves a cyclic two step reaction which is performed in a DNA thermal cycler machine. The first step is a high temperature melting step in which double stranded DNA unwinds to become single stranded. The second step is a cooling step in which two sets of adjacent, complementary oligonucleotides anneal to the single stranded target DNA molecules and are ligated together by a DNA ligase enzyme. The products of ligation from one cycle serve as templates for the ligation reaction of the next cycle. Thus, LCR results in the exponential amplification of ligation products.

MATERIALS AND METHODS

The materials used in this experiment were obtained from Stratagene, La Jolla, Calif. The optimal temperature for the second step of the LCR cycle, in which the oligonucleotides are annealed to the DNA target molecules, was determined empirically by the use of the gradient thermal cycler of the invention. Two sets of reactions were set up, one with a wild type template to which the oligonucleotides were complementary, and one with a mutant template that differed from the wild type template DNA sequence by one base transition. The DNA templates used in this experiment were plasmid constructs containing the pBluescriptII vector and the lac I gene. The wild-type template contained a normal lac I sequence, and the mutant template contained a C to T transition mutation at site 191 within the insert. The four oligonucleotide probes consisted of two pairs of two oligonucleotides each. The first set, A and B, were adjacent to each other and complementary to one strand of the target DNA. The second set, C and D, were complementary to the first set, and therefore occupied adjacent sites on the second strand of the target DNA. The oligonucleotide probe sequences (5' to 3') were as follows:

| | | | | |
|---|---|---|---|---|
| A: | TTGTGCCACG | CGGTTGGGAA | TGTA | (SEQ ID NO:5) |
| B: | AGCAACGACT | GTTTGCCCGC | CAGTTC | (SEQ ID NO:6) |
| C: | TACATTCCCA | ACCGCGTGGC | ACAAC | (SEQ ID NO:7) |
| D: | AACTGGCGGG | CAAACAGTCG | TTGT | (SEQ ID NO:8) |

Oligonucleotide probes A and D were 5'-phosphorylated during synthesis. The sequence of the wild type lac I insert, starting at site 161 of the insert, was as follows:

5' CTGAATTACA TTCCCAACCG CGTGGCACAA CAACTGGCGG
GCAAACAGTC GTTGCTGATT 3' (SEQ ID NO:9)

The mutant sequence differed from the wild type by a C to T transition at site 191. The LCR experiment was performed as follows: The following ingredients were combined in a sterile 500 μl of 10XZ Pfu LCR buffer, 15 μl of sterile dH$_2$O, 1 μl (10 ng of each) of oligonucleotide mixture, 1 μl (100 pg) of either the wild-type or mutant plasmid templates or no template, and 1 μl (4U) of Pfu DNA ligase enzyme. A 25 μl overlay of sterile mineral oil was added to the tube. This procedure was repeated so that there were a total of 5 tubes each of either the wild type template reaction mixture or the mutant template reaction mixture. The tubes were placed in the gradient thermal cycler of the invention in positions 1, 3, 5, 7 and 8, so that at each isothermal column in the machine, there would be a wild type and a mutant template reaction. The machine was programmed to cycle between a high temperature of 92° C. and the gradient block, which was varied in temperature between 56° C. and 70° C. The machine was programmed to move to the high temperature block for 4 minutes, then the gradient block for 3 minutes, then to move between the high temperature block and the gradient block 25 times, stopping for 1 minute at each block. The ligation chain reaction products were visualized by electrophoresis on a 6% polyacrylamide get buffered with TBE, followed by staining with ethidium bromide and photography under UV light.

RESULTS

The wild type template reaction produced the most intense positive signal in position 8, which corresponds to the coldest (56° C.) section of the gradient block. The use of the gradient thermal cycler of the invention allowed the empirical determination of the best annealing temperature for this reaction in one experiment.

There are many modifications and variations of the thermal gradient block which can advantageously be incorporated into it or related structures. Further, multiple thermal gradient blocks could be employed as more than one block of a multi-block thermal cycler where samples are automatically moved between the various blocks, thereby allowing for multiple reactions to be operated at multiple temperatures.

The invention has been described in detail with respect to its use with PCR. However, in addition to being exceptionally useful for the determination of the optimal temperature for individual steps in a PCR procedure, the invention is also useful for determining the optimal temperature for numerous other chemical reactions. These other chemical reactions include any non-PCR nucleic acid amplification that employs an annealing step analogous to a PCR annealing step, such as ligase chain reaction (LCR) and DNA cycle sequencing. Other types of reactions for which the invention will be useful include DNA sequencing, cDNA synthesis using a cycling reaction, coupled amplification sequencing (CAS), rapid amplification of cDNA ends (RACE) and any other incubation reaction in which incubations must be accomplished at multiple temperatures.

What is claimed is:

1. An apparatus for generating a temperature gradient across a heat conducting block comprising:
- a reaction mixture holder including a heat conducting block having top and bottom portions, first and second opposing end portions, and opposing side walls extending between said opposing end portions;
- said heat conducting block having a plurality of reaction mixture wells formed in said top portion and spaced across said top portion in parallel rows;
- said heat conducting block having holes bored therethrough between the rows of wells and extending through the block between said side walls;
- a first block heater positioned adjacent to said first opposing end portion; and
- a block cooler positioned adjacent to said second opposing end portion.

2. An apparatus as recited in claim 1 wherein said heat conducting block is composed of brass.

3. An apparatus as recited in claim 1 wherein said block cooler is a heat sink attached to the second opposing end portion of said heat conducting block.

4. An apparatus as recited in claim 3 wherein said block cooler further comprises a fan positioned adjacent to said heat sink.

5. An apparatus as recited in claim 1 further comprising a second block heater positioned adjacent to said bottom portion, and means for independently controlling said first and second block heaters.

6. An apparatus for performing molecular biological reactions comprising:
- a temperature-gradient block having a plurality of rows of reaction mixture wells formed in a top portion thereof, wherein said temperature-gradient block has first and second opposing end portions and opposing side walls extending between said opposing end portions;
- said temperature-gradient block having holes bored therethrough between the rows of wells and extending through the block between said side walls; and
- means for generating a temperature gradient between said first and second opposing end portions of the temperature-gradient block.

7. An apparatus according to claim 6 wherein said temperature-gradient block is composed of brass.

8. An apparatus according to claim 6 further comprising a heating means for heating a bottom portion of said temperature-gradient block.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

CCTGAGGGCT CCCAGAGAGT GG     22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GGTTTAGCAC GACCACAACA GC     22

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

AGTCAGGTAT CTTTGACAGT     20

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

AAGCTTCAGG AAAACAGTGA GCAGCGCCTC                                                                 30

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

TTGTGCCACG CGGTTGGGAA TGTA                                                                       24

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

AGCAACGACT GTTTGCCCGC CAGTTC                                                                     26

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

TACATTCCCA ACCGCGTGGC ACAAC                                                                      25

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

AACTGGCGGG CAAACAGTCG TTGT                                                                       24

(2) INFORMATION FOR SEQ ID NO:9:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
CTGAATTACA TTCCCAACCG CGTGGCACAA CAACTGGCGG GCAAACAGTC GTTGCTGATT      60
```